United States Patent
Thakur et al.

(10) Patent No.: US 9,555,129 B2
(45) Date of Patent: Jan. 31, 2017

(54) ADENOSINE DERIVATIVE FORMULATIONS FOR MEDICAL IMAGING

(75) Inventors: Ajit B. Thakur, East Brunswick, NJ (US); Dianne D. Zdankiewicz, North Billerica, MA (US); Hsun-Wen Hsu, North Billerica, MA (US); James F. Castner, North Billerica, MA (US); James E. Anderson, North Billerica, MA (US)

(73) Assignee: ADENOSINE THERAPEUTICS, LLC, Charlottesville, VA (US)

( * ) Notice: Subject to any disclaimer, the term of this patent is extended or adjusted under 35 U.S.C. 154(b) by 421 days.

(21) Appl. No.: 13/615,760

(22) Filed: Sep. 14, 2012

(65) Prior Publication Data

US 2013/0004426 A1   Jan. 3, 2013

Related U.S. Application Data

(63) Continuation of application No. 12/014,949, filed on Jan. 16, 2008.

(60) Provisional application No. 60/885,489, filed on Jan. 18, 2007.

(51) Int. Cl.
*A61M 36/14* (2006.01)
*A61K 51/00* (2006.01)
*A61K 47/48* (2006.01)
*A61K 49/00* (2006.01)
*B82Y 5/00* (2011.01)

(52) U.S. Cl.
CPC ..... *A61K 47/48969* (2013.01); *A61K 49/0002* (2013.01); *B82Y 5/00* (2013.01)

(58) Field of Classification Search
CPC ................ A61K 47/48969; A61K 49/0002; B82Y 5/00
USPC ........................................................ 424/1.11
See application file for complete search history.

(56) References Cited

U.S. PATENT DOCUMENTS

| 6,322,771 | B1 * | 11/2001 | Linden et al. | 424/9.3 |
| 7,115,586 | B2 * | 10/2006 | Loftsson | 514/58 |
| 2008/0064653 | A1 * | 3/2008 | Li et al. | 514/46 |

OTHER PUBLICATIONS

Uekama et al. Chem. Rev. 1998, 98, 2045-2076.*
Gomori. Methods in Enzymology 1955, 138-146.*

* cited by examiner

*Primary Examiner* — Michael G Hartley
*Assistant Examiner* — Sean R Donohue
(74) *Attorney, Agent, or Firm* — Vance Intellectual Property PC

(57) ABSTRACT

A stable composition useful for myocardial perfusion imaging contains one or more 2-alkynyladenosine derivatives; and a solvent which is made up of water and hydroxypropyl-β-cyclodextrin.

12 Claims, 1 Drawing Sheet

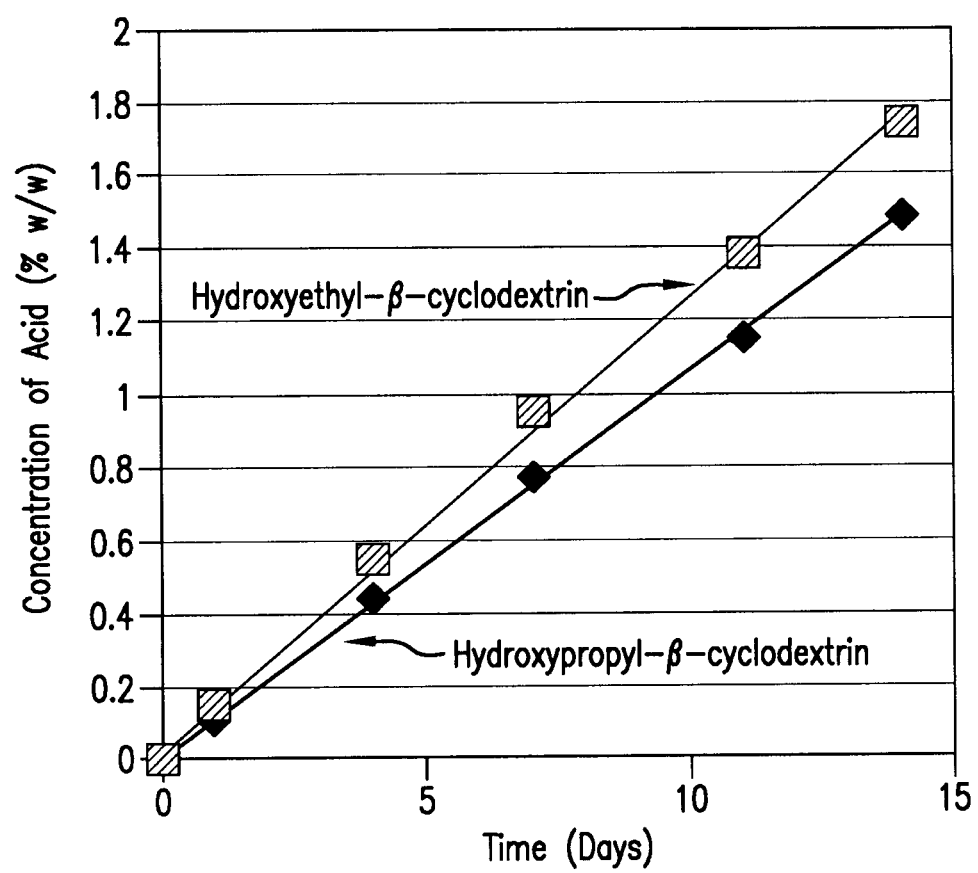

ADENOSINE DERIVATIVE FORMULATIONS FOR MEDICAL IMAGING

CROSS-REFERENCE TO RELATED APPLICATIONS

This application is a continuation of U.S. patent application Ser. No. 12/014,949 filed Jan. 16, 2008, which claims the benefit of U.S. Provisional Application No. 60/885,489, filed 18 Jan. 2007, which is expressly incorporated fully herein by reference.

FIELD OF THE INVENTION

The present invention relates to novel formulations of adenosine derivatives which are storage stable and useful for medical imaging, in particular myocardial perfusion imaging.

BACKGROUND OF THE INVENTION

Adequate coronary vasodilation is essential to myocardial perfusion imaging. Coronary vasodilation increases coronary blood flow. This increase creates differences in the distribution of the imaging agent great enough to identify regions supplied by stenosed coronary vessels and to distinguish problem areas from healthy tissue.

Exercise stress testing often is employed for dilating coronary vessels, hence increasing coronary blood flow. However, maximum exercise levels are often required for sufficient vasodilation, and exercise capacity varies greatly among patients. Many patients absolutely cannot exercise to any satisfactory level, due to peripheral vascular disease, medications, poor patient motivation, and a variety of other coexisting conditions. Therefore, exercise may not always be an option.

The compound adenosine, having the formula $C_{10}H_{13}N_5O_4$, is known to be highly efficacious as a pharmacologic stress agent for myocardial imaging in patients which are unable to exercise adequately. This compound has consistently produced maximum vasodilation of coronary arteries, with relatively minimal side effects. Adenosine is typically administered intravenously to a patient at rest, and its pharmacological action then mimics some degree of physical assertion. The short half-life of adenosine is responsible for its short-acting pharmacological effects, making it extremely useful for diagnostic evaluation and risk assessment in coronary artery disease. The attending physician can quickly image the diseased coronary area, and thereafter the adenosine and any adjunct compounds are broken down or evacuated from the body.

Other adenosine-based analogs and derivatives have now shown great potential as possible coronary vasodilators for use in medical imaging. Many of these compounds have been set forth and identified in U.S. Pat. No. 6,232,297. This patent sets forth a new class of 2-alkynyladenosine derivatives.

Unfortunately, many adenosine derivatives can be very difficult to solubilize in aqueous media. There are also long-range stability issues associated with adenosine-based formulations. To address this issue, the skilled artisan has often turned to solvents like glycerol, propylene glycol and other polar additives when preparing injection solutions. Alternatively, β-cyclodextrin, because of its unique donut-shape, has been shown to form inclusion complexes with sparingly soluble and unstable drugs. The action of β-cyclodextrin significantly stabilizes and increases the water-solubility of many pharmacological compounds.

U.S. Pat. No. 6,407,079 describes many β-cyclodextrin derivatives which are set forth as being particularly useful as complex forming agents to solubilize and stabilize active compounds. These include hydroxyethyl, hydroxypropyl and dihydroxypropyl ether, their corresponding mixed ethers, and further mixed ethers with methyl or ethyl groups, such as methyl-hydroxyethyl, methyl-hydroxypropyl, ethyl-hydroxyethyl and ethyl-hydroxypropyl ether of β-cyclodextrin.

However, stability issues may still persist with one or more of these compounds. What is therefore needed in the art is an improved composition containing one or more adenosine derivatives, together with a suitable solvent, that is highly useful in myocardial perfusion imaging, and is also storage stable for extended periods. Also needed in the art is a method for enhancing cardiovascular imaging by administering an improved cardiovascular stress formulation to a patient.

SUMMARY OF THE INVENTION

The invention in a first embodiment is directed to a stable composition useful for myocardial perfusion imaging, comprising one or more 2-alkynyladenosine derivatives, and a solvent consisting essentially of water and hydroxypropyl-β-cyclodextrin (which may also be referred to herein as hydroxypropylether-β-cyclodextrin).

In a further embodiment, there is provided a method of inducing cardiovascular stress for medical imaging purposes, which involves administering to a patient a pharmacologic vasodilation formulation, comprising one or more adenosine analogs, a solvent consisting essentially of water and hydroxypropyl-β-cyclodextrin, and a buffer.

More specifically, the invention provides a stable, adenosine-analog based composition, comprising:
  (a) an adenosine derivative, which is methyl trans-4-[3-[6-amino-9-(N-ethyl-β-D-ribofuranosyluronamide)-9H-purin-2-yl]prop-2-ynyl]cyclohexane carboxylate or a pharmaceutically acceptable salt thereof;
  (b) a solvent consisting essentially of water and hydroxypropyl-β-cyclodextrin;
  (c) sodium citrate; and
  (d) citric acid.

In addition, the invention includes a kit useful for cardiovascular stress testing, containing as components one or more 2-alkynyladenosine derivatives, and a solvent consisting essentially of water and hydroxypropyl-β-cyclodextrin.

The present invention is directed to these, as well as other important ends, hereinafter described.

BRIEF DESCRIPTION OF THE DRAWINGS

FIG. 1 shows a plot of the amount of the acid (% w/w relative to the adenosine derivative) formed as a function of time (days) for adenosine derivative solutions using either hydroxypropyl-β-cyclodextrin or hydroxyethyl-β-cyclodextrin.

DETAILED DESCRIPTION OF THE PREFERRED EMBODIMENTS

The adenosine analogs or derivatives which are useful as part of the invention are set forth in U.S. Pat. No. 6,232,297, which is incorporated in its entirety herein by reference. Preferred are 2-alkynyladenosine derivatives. Of these, those which are substituted at the ethyne position by substituted cycloalkyl moieties are more preferred. Even more desirably, the riboside residue at the 5'-position ("X" below) is substituted by an N-alkyl- (or cycloalkyl) carboxyamino ("aminocarbonyl") moiety.

In particular, the compounds of the invention have the following general formula (I):

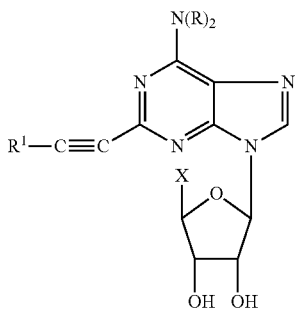

wherein each R is individually hydrogen, $C_1$-$C_6$ alkyl, $C_3$-$C_7$ cycloalkyl, phenyl or phenyl($C_1$-$C_3$)-alkyl;

X is —$CH_2OH$, —$CO_2R^2$, —$OC(O)R^2$, $CH_2OC(O)R^2$ or $C(O)NR^3R^4$;

each of $R^2$, $R^3$ and $R^4$ is individually H, $C_{1-6}$-alkyl, or $C_{1-6}$-alkyl substituted with 1-3 $C_{1-6}$-alkoxy, $C_3$-$C_6$ cycloalkyl, $C_{1-6}$-alkylthio, halogen, hydroxy, amino, mono ($C_{1-6}$-alkyl)amino, di($C_{1-6}$-alkyl)amino, or $C_{6-10}$-aryl, wherein aryl may be substituted with 1-3 halogen, $C_{1-6}$-alkyl, hydroxy, amino, mono($C_{1-6}$-alkyl)amino, or di($C_{1-6}$-alkyl)amino; $C_{6-10}$-aryl; or $C_{6-10}$-aryl substituted with 1-3 halogen, hydroxy, amino, mono($C_{1-6}$-alkyl)amino, di($C_{1-6}$-alkyl)amino or $C_{1-6}$-alkyl;

$R^1$ is (X—(Z)—)$_n$[($C_3$-$C_{10}$)cycloalkyl]-(Z')—, wherein Z and Z' are individually ($C_1$-$C_6$)alkyl, optionally interrupted by 1-3 S or nonperoxide O, or are absent; and, n is 1-3; or a pharmaceutically acceptable salt thereof.

Of the foregoing, particularly preferred are compounds wherein 5'-X is $CH_2OH$ or —$C(O)NR^3R^4$. More preferred is the —$C(O)NR^3R^4$ moiety. Z' is preferably —$CH_2$ or $CH_2$—$CH_2$. $C_3$-$C_{10}$ cycloalkyl is preferably cyclohexyl or cyclopentyl. X is preferably $C_1$-$C_4$ alkoxycarbonyl, $C(O)R^3R^4$ or acetoxymethyl.

More highly preferred compounds useful as part of the invention include those of formula (I) above wherein each R is H, X is ethylaminocarbonyl and $R^1$ is 4-carboxycyclohexylmethyl, $R^1$ is 4-methoxycarbonylcyclohexylmethyl or $R^1$ is 4-acetoxymethylacyclohexylmethyl. These are set forth below:

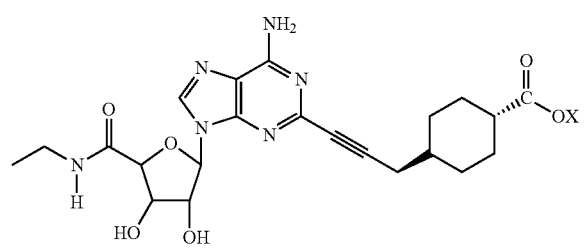

-continued

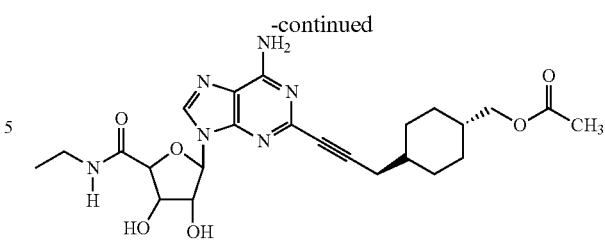

wherein, acid, X=H and ester, X=methyl.

Particularly useful as part of the invention is the compound identified above as methyl trans-4-[3-[6-amino-9-(N-ethyl-β-D-ribofuranosyluronamide)-9H-purin-2-yl]prop-2-ynyl]cyclohexane carboxylate or a pharmaceutically acceptable salt thereof.

One or more of the adenosine analogs described above typically comprise about 0.001 to 10% w/v of the composition of the invention, more preferably about 0.005 to 1% w/v of the final formulation. It is preferred that the adenosine derivative be present in an amount within the range of about 25 to 150 μg/mL of the final formulation, and even more desirably about 50 to 125 μg/mL. Described yet another way, the adenosine derivatives herein utilized can be included in an amount to deliver a dose not exceeding about 5 mcg/kg of body weight, more preferably not exceeding about 2 mcg/kg of body weight. However, it is expected that the final amount of adenosine-based compound may be optimized by the medical practitioner so as to suit the particular needs of a patient.

Further included as part of the invention, with one or more of the adenosine derivatives described above, is a solvent. The solvent is preferably aqueous-based. More preferably, the solvent contains water and the inclusion forming compound hydroxypropyl-β-cyclodextrin, which may also be referred to as hydroxypropylether-β-cyclodextrin. This compound has been described in U.S. Pat. No. 6,407,079, which is incorporated herein by reference. However, it has now been shown that of the substituted β-cyclodextrins, hydroxypropyl-β-cyclodextrin is especially efficacious in solubilizing and stabilizing the adenosine derivatives. In particular, hydroxypropyl-β-cyclodextrin is preferred over hydroxyethyl-β-cyclodextrin (also referred to as hydroxyethylether-β-cyclodextrin), as well as other substituted β-cyclodextrins, in particular other substituted ether β-cyclodextrins. Hydroxypropyl-β-cyclodextrin is also preferred over other solvents such as unsubstituted β-cyclodextrin, δ-cyclodextrin, propylene glycol, and Captisol (another substituted β-cyclodextrin). Thus, it is highly preferred that no other solubility enhancers other than hydroxypropyl-β-cyclodextrin, in particular other β-cyclodextrins, be included in the final composition, other than residual or trace amounts that might remain after normal processing.

Examples of the concentration of hydroxypropyl-β-cyclodextrin include being within the range of about 0.1-10% w/v, about 0.5 to 2% w/v, and about 1% w/v of the final formulation. One example of the molar ratio of the adenosine derivative to hydroxypropyl-β-cyclodextrin is within the range of about 1:30 to 1:150.

Water can comprise the remainder of the solvent, and by extension, the remainder of the final formulation, but for optional additional excipients.

Certain excipients, such as buffers, for example, also may be included in the composition of the invention. Buffers act as pH control agents, and can include such compounds as citric acid, sodium citrate, or both. Other buffers available to the skilled artisan may also be utilized. Other excipients such as preservatives and rheology agents, for example, may also be included, if desired. The additional excipient(s) together can comprise from about 0.001 to 1% w/v of the final composition.

In another embodiment, hydroxyethyl-β-cyclodextrin is absent from the composition of the invention. In another embodiment, any other β-cyclodextrin is absent from the composition of the invention. In another embodiment, any other solvent is absent from the composition of the invention.

To prepare the composition of the invention, the adenosine derivative may be admixed with the solvent, and any additional excipients. The solvent may be first prepared by admixing the water and hydroxypropyl-β-cyclodextrin. A dosage form may be prepared as set forth in the art, such as a sealed bolus, vial or syringe using materials that are readily available. The composition of the invention may also be assembled into a ready-to-use kit, with one or more dosage units contained therein.

The composition of the invention is highly storage stable for extended periods. Preferably, in sealed form, the composition can remain efficacious for up to at least about three (3) months, and more preferably up to about six (6) months. It is desirable that the composition remain storage stable for periods of up to about one (1) year, and even more desirably up to at least about two (2) years, or even longer.

Further provided as part of the invention is a method of cardiovascular imaging using a stress-inducing, pharmacologic agent, comprising administering to a patient a formulation according to the present invention, containing one or more adenosine derivatives as heretofore described, together with the solvent, and any excipients, as also described. Preferably, the composition is administered intravenously by a skilled practitioner such as a doctor, physician's assistant, or nurse practitioner using procedures established in the art. Other methods of administration may be contemplated by the skilled artisan. The composition is administered in a dose and at a rate which will allow the practitioner to then obtain a readable image of the myocardial region of interest. The image is obtained using methods available in the art.

In a preferred embodiment, the composition of the invention is administered in a dose which does not exceed about 5 mcg adenosine derivative per kilogram of patient body weight. More preferably, the dosage is such that the amount of administered adenosine derivative does not exceed about 2 mcg/kg. of patient body weight. Even more desirably, the composition is administered in a dose of between about 0.05 and 5 mcg/kg of patient body weight.

EXAMPLES

The following examples are provided to illustrate various preferred aspects of the invention, and should not be construed as limiting the scope thereof:

Example 1

The following composition was prepared as hereinabove described:

| Components | Amount or Description |
| --- | --- |
| Methyl trans-4-[3-[6-amino-9-(N-ethyl-β-D-ribofuranosyluronamide)-9H-purin-2-yl]prop-2-ynyl]cyclohexane carboxylate | 100 μg/mL |
| Sodium Citrate Buffer | 10 mM at pH 4.8 ± 0.2 |
| Hydroxypropyl-β-Cyclodextrin (CAS 128446-35-5) (Hydroxypropyl Betadex [USP]) | 2% by weight |
| WFI (water for injection) | Q.S. |
| Headspace | Air |
| Fill Volume | 3 mL |

After preparation, the above formulation was aluminum crimp-sealed in a 5 cc tubing vial, and closed with a 20 mm serum stopper. Also prepared was a formulation containing 50 μg/mL of active substance, together with 1% by weight of hydroxypropyl-β-cyclodextrin.

Example 2

The present study established the bioequivalency of the pharmacokinetic parameters for one formulation according to a preferred embodiment of the invention versus another formulation in an anesthetized open chest canine model using the same adenosine analog. Five female mongrel dogs, 1.5-2 years of age (11-15 kg) were used. After surgical instrumentation and a stabilization period, each dog received a bolus intravenous injection of adenosine (300 μg/kg) as a reference control followed by four intravenous doses (non-cumulative) of Formulation 1 (the invention) and Formulation 2 (a lyophilized formulation) (two 1 μg/kg doses of each formulation). Blood samples were collected at 0 (pre-dose), 1, 3, 5, 7, 10, 15 and 30 minutes post-injection of each dose for determination of plasma levels of the active drug substance adenosine analog and the carboxylic acid metabolite by LC/MS/MS. Pharmacokinetic (PK) analysis included $C_{max}$, area under the time-plasma concentration curve (AUC), clearance (CL), volume of distribution at steady state ($V_{dss}$) and terminal ((R), phase) half-life ($t_{1/2}$). Hemodynamic responses, expressed as a percent change from baseline values, for each dose level included measurements of coronary blood flow, arterial blood pressure, heart rate, left ventricular systolic pressure and +dP/dt. Bioequivalence was determined using log transformation of the data. The two adenosine analog formulations were considered to be bioequivalent if the 90% confidence interval for the ratio of the formulation means for AUC of adenosine analog and the carboxylic acid metabolite was within 0.8 and 1.25.

The plasma levels of adenosine analog and the carboxylic acid metabolite of Formulations 1 and 2 had nearly identical profiles. The 90% confidence intervals for the ratio of AUC (0-last) for adenosine analog and for the carboxylic acid metabolite were 1.02 to 1.15 and 0.94 to 1.16, respectively, which were within the acceptable limits of 0.8 to 1.25 to demonstrate bioequivalence. Additional pharmacokinetic parameters for adenosine analog (AUC(0-∞), CL, $C_{max}$, $t_{1/2}$, $Vd_{ss}$) and the carboxylic metabolite ($C_{max}$, $t_{1/2}$) also met the bioequivalence criterion.

Administration of both Formulations 1 and 2 at 1 μg/kg caused similar pharmacodynamic changes. There were no significant differences, respectively, on increase in mean coronary blood flow (147.5% vs. 160.4%), duration of coronary blood flow increase≥150% of baseline (5.7 vs. 5.0 minutes), decrease in mean arterial blood pressure (23.3% vs. 23.6%), increase in heart rate (11.3% vs. 12.2%), increase in left ventricular systolic pressure (9.0% vs. 6.0%) and increase in +dP/dt (46.3% vs. 45.4%). These findings are consistent with Formulations 1 and 2 being equivalent.

Based on the pharmacokinetic assessment, the results of this study demonstrated that the Formulations 1 and 2 are bioequivalent and both are capable of inducing increased coronary blood flow in the anesthetized open chest dog.

Example 3

This example illustrates the comparative stability of adenosine derivative compositions using hydroxypropyl-β-cyclodextrin as part of the invention, versus those containing hydroxyethyl-β-cyclodextrin.

A solution of methyl trans-4-[3-[6-amino-9-(N-ethyl-β-D-ribofuranosyluronamide)-9H-purin-2-yl]prop-2-ynyl]cyclohexane carboxylate at 50 μg/mL was prepared in 10 mM citrate buffer at pH 4.8 with 1% (w/v) of hydroxypropyl-β-cyclodextrin. A similar solution was prepared except that the 1% (w/v) hydroxypropyl-β-cyclodextrin was replaced with 1% (w/v) hydroxyethyl-β-cyclodextrin. Both solutions were stored at 70° C. for a period of fourteen days. The stability of the adenosine derivative was evaluated over the fourteen day period using chromatography to measure the increase in the primary degradation product, which is generated by hydrolysis of the methyl ester to form the acid by the reaction shown below.

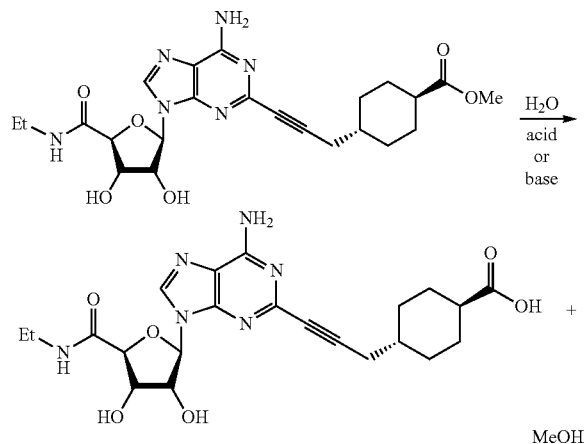

A plot of the amount of the acid (% w/w relative to the adenosine derivative) formed as a function of time (days) is shown in FIG. 1 for the adenosine derivative solutions using either hydroxypropyl-β-cyclodextrin or hydroxyethyl-β-cyclodextrin. The plot clearly demonstrates that the rate of formation of the acid complex is lower when the stabilizing agent is hydroxypropyl-β-cyclodextrin relative to hydroxyethyl-β-cyclodextrin. For example, after fourteen days the amount of acid is 1.5% (w/w) using hydroxypropyl-β-cyclodextrin and is 1.7% (w/w) using hydroxyethyl-β-cyclodextrin.

Various modifications of the invention, in addition to those described herein, will be apparent to those skilled in the art from the foregoing description. Such modifications are also intended to fall within the scope of the appended claims.

What is claimed:

1. A stable composition useful for myocardial perfusion imaging, comprising:
    (a) an adenosine derivative, which is methyl trans-4-[3-[6-amino-9-(N-ethyl-β-D-ribofuranosyluronamide)-9H-purin-2-yl]prop-2-ynyl]cyclohexane carboxylate or a pharmaceutically acceptable salt thereof; and,
    (b) a solvent consisting essentially of water and hydroxypropyl-β-cyclodextrin.

2. The composition of claim 1, further comprising a buffer.

3. The composition of claim 2, wherein the buffer comprises: sodium citrate and citric acid.

4. The composition of claim 1, wherein the concentration of hydroxypropyl-β-cyclodextrin is about 0.1-10% w/v.

5. The composition of claim 4, wherein the concentration of hydroxypropyl-β-cyclodextrin is about 0.5-2% w/v.

6. The composition of claim 1, wherein the molar ratio of the adenosine derivative to hydroxypropyl-β-cyclodextrin is about 1:30 to 1:150.

7. The composition of claim 1, wherein hydroxyethyl-β-cyclodextrin is absent from the composition.

8. The composition of claim 1, wherein any other β-cyclodextrin is absent from the composition.

9. The composition of claim 1, wherein any other solvent is absent from the composition.

10. The composition of claim 1, wherein the composition is storage stable for at least about 3 months.

11. A cardiovascular stress testing kit, comprising:
    (a) an adenosine derivative, which is methyl trans-4-[3-[6-amino-9-(N-ethyl-β-D-ribofuranosyluronamide)-9H-purin-2-yl]prop-2-ynyl]cyclohexane carboxylate or a pharmaceutically acceptable salt thereof; and,
    (b) a solvent consisting essentially of water and hydroxypropyl-β-cyclodextrin.

12. The kit of claim 11, wherein hydroxyethyl-β-cyclodextrin is absent from the solvent.

* * * * *